(12) United States Patent
Daum et al.

(10) Patent No.: US 11,701,076 B2
(45) Date of Patent: Jul. 18, 2023

(54) OPERATING DEVICE FOR A MEDICAL SYSTEM FOR IMAGING AND/OR INTERVENTION

(71) Applicant: Siemens Healthcare GmbH, Erlangen (DE)

(72) Inventors: Arnulf Daum, Bayreuth (DE); Kay Uwe Seemann, Emskirchen (DE); Thorsten Büttner, Pretzfeld (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/530,659

(22) Filed: Nov. 19, 2021

(65) Prior Publication Data

US 2022/0160318 A1 May 26, 2022

(30) Foreign Application Priority Data

Nov. 26, 2020 (DE) ...................... 20 2020 106 821.0

(51) Int. Cl.
*A61B 6/00* (2006.01)
*A61B 6/04* (2006.01)
*A61B 6/03* (2006.01)

(52) U.S. Cl.
CPC ............ *A61B 6/467* (2013.01); *A61B 6/0407* (2013.01); *A61B 6/548* (2013.01); *A61B 6/032* (2013.01); *A61B 6/037* (2013.01)

(58) Field of Classification Search
CPC ........ A61B 6/467; A61B 6/0407; A61B 6/548; A61B 6/032; A61B 6/037; A61B 6/56
See application file for complete search history.

(56) References Cited

U.S. PATENT DOCUMENTS

2021/0219927 A1* 7/2021 Dencovski ........... A61B 8/4218

FOREIGN PATENT DOCUMENTS

CA 2918102 C * 6/2018 ............. B62K 23/06
WO WO-2017214985 A1 * 12/2017 ........... B64C 39/024

* cited by examiner

*Primary Examiner* — David P Porta
*Assistant Examiner* — Casey Bryant
(74) *Attorney, Agent, or Firm* — Harness, Dickey & Pierce, P.L.C.

(57) ABSTRACT

An operating device for a medical system for imaging and/or intervention is disclosed. In an embodiment, the operating device includes a housing; a grip region; a coupling unit; and a connecting unit. The connecting unit is configured to releasably connect to a holding structure for the operating device and, via the coupling unit, is coupled to the grip region such that a releasing of a releasable connection is caused by a gripping of the grip region with one hand of a person and an establishing of the releasable connection is caused by a letting go of the grip region. Further, the grip region is configured for carrying of the operating device by a gripping the grip region with one hand of the person.

24 Claims, 5 Drawing Sheets

OPERATING DEVICE FOR A MEDICAL SYSTEM FOR IMAGING AND/OR INTERVENTION

PRIORITY STATEMENT

The present application hereby claims priority under 35 U.S.C. § 119 to German patent application numbers DE 202020106821.0 filed Nov. 26, 2020, the entire contents of which are hereby incorporated herein by reference.

FIELD

Example embodiments of the invention generally relate to an operating device for a medical system for imaging and/or intervention. Example embodiments of the invention further generally relate to a medical system for imaging and/or intervention.

BACKGROUND

A medical system for imaging and/or intervention may have an operating device, for example for controlling one or more components of the medical system. Particularly in a situation involving an intervention, it may be advantageous if the operating device can be assembled on a holding structure with relatively little effort, and disassembled accordingly.

SUMMARY

At least one embodiment of the invention provides an operating device for a medical system for imaging and/or intervention, of which the handling is improved, particularly with regard to assembly on a holding structure and a corresponding disassembly.

At least one embodiment of the invention relates to an operating device for a medical system for imaging and/or intervention, wherein the operating device has a housing, a grip region, a coupling unit and a connecting unit, wherein the connecting unit is configured for releasably connecting to a holding structure for the operating device and, via the coupling unit, is coupled to the grip region such that a releasing of the releasable connection is caused by gripping the grip region with one hand and an establishing of the releasable connection is caused by letting go of the grip region, and wherein the grip region is embodied such that the operating device can be carried in one hand by gripping the grip region with one hand.

At least one embodiment of the invention further relates to a medical system for imaging and/or intervention, having the operating device according to one of the disclosed embodiments and the holding structure for the operating device.

At least one embodiment of the invention further relates to an operating device for a medical system for at least one of imaging and intervention, comprising:

a housing;
a grip region;
a coupling unit; and
a connecting unit,
wherein the connecting unit is configured to releasably connect to a holding structure for the operating device and, via the coupling unit, is coupled to the grip region such that a releasing of a releasable connection is caused by a gripping of the grip region with one hand of a person and an establishing of the releasable connection is caused by a letting go of the grip region, and wherein the grip region is configured for carrying of the operating device by a gripping the grip region with one hand of the person.

At least one embodiment of the invention further relates to a medical system for at least one of imaging and intervention, comprising:

the operating device of an embodiment; and
the holding structure for the operating device.

BRIEF DESCRIPTION OF THE DRAWINGS

The invention will be explained below based upon example embodiments with reference to the accompanying figures. The representation in the figures is schematic, greatly simplified and not necessarily to scale.

In the figures.

DETAILED DESCRIPTION OF THE EXAMPLE EMBODIMENTS

Figure 1:
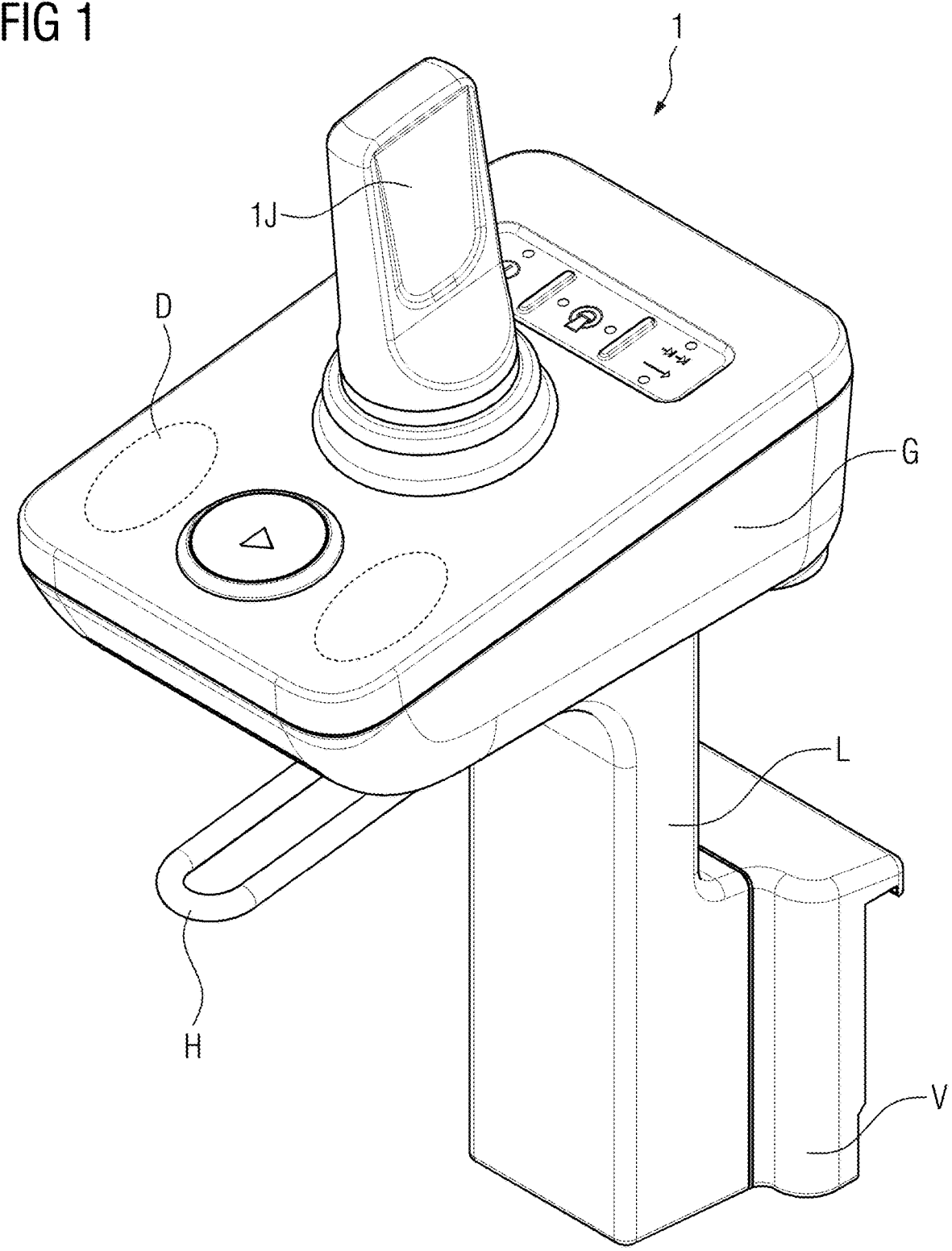
FIG. 1 shows an operating device for a medical system for imaging and/or intervention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an operating device for a medical system for imaging and/or intervention, wherein the operating device has a housing, a grip region, a coupling unit and a connecting unit, wherein the connecting unit is configured for releasably connecting to a holding structure for the operating device and, via the coupling unit, is coupled to the grip region such that a releasing of the releasable connection is caused by gripping the grip region with one hand and an establishing of the releasable connection is caused by letting go of the grip region, and wherein the grip region is embodied such that the operating device can be carried in one hand by gripping the grip region with one hand.

The releasable connection may in particular comprise a mechanically releasable connection. The mechanically releasable connection may be configured, for example, to mechanically fix the operating device relative to the holding structure.

For example, the operating device may be a portable operating device, in particular an operating device that can be carried in one hand. The operating device may be configured, for example, for operating, in particular remotely controlling, one or more components of the medical system.

In this manner, a one-handed handling of the operating device is enabled, in particular for implementation between the various connecting points of the holding structure.

One embodiment provides that the releasable connection is a releasable clamp connection.

One embodiment provides that the operating device further has a lever that is mounted such that it can pivot relative to the housing, wherein the grip region has a region of the housing and a region of the lever, which are arranged relative to one another such that gripping the grip region with one hand causes a pivoting of the region of the lever toward the region of the housing, and wherein the connecting unit is coupled to the grip region via the coupling unit such that, by pivoting the region of the lever toward the region of the housing, a force is exerted on the connecting unit which causes the releasing of the releasable connection.

It may furthermore be provided that letting go of the grip region causes a pivoting of the region of the lever away from the region of the housing and/or that the connecting unit is coupled to the grip region via the coupling unit such that, by pivoting the region of the lever away from the region of the housing, a force is exerted on the connecting unit which causes the establishing of the releasable connection.

It may furthermore be provided that the region of the housing has a contact area such that, when the grip region is gripped with one hand, a thumb of a hand is pressed against the contact area and at least one finger of the hand opposite the thumb of the hand is pressed against the region of the lever.

One embodiment provides that the coupling unit is embodied for mechanical force transfer, for example of a tensile force and/or a compressive force, from the grip region to the connecting unit.

One embodiment provides that the coupling unit has a linkage.

As an alternative or in addition, the coupling may, for example, have a Bowden cable and/or a pneumatic or hydraulic line.

It may furthermore be provided that the coupling unit has a sensor, a signal line and an actuator. In particular, the sensor may be configured to generate a signal based on the one-handed gripping of the grip region. The signal line may be configured, in particular, to transfer the signal from the sensor to the actuator. In particular, the actuator may be configured to drive the connecting unit based on the signal.

One embodiment provides that the operating device further has a column-shaped section, wherein the grip region and the connecting unit are interconnected via the column-shaped section such that the grip region and the connecting unit are spaced apart from one another in relation to a direction that is substantially parallel, in particular is parallel, with a column axis of the column-shaped section.

The column-shaped section may, for example, be substantially cylindrical, in particular cylindrical, and/or substantially prism-shaped, in particular prism-shaped. The column axis of the column-shaped section may, for example, be a cylinder axis and/or be parallel with a peripheral surface of the column-shaped section.

It may furthermore be provided that, in addition to the column-shaped section, at least one further section is arranged between the grip region and the connecting unit. The at least one further section may be arranged, for example, between the grip region and the column-shaped section and/or between the column-shaped section and the connecting unit.

It may furthermore be provided that the column-shaped section is at least 3 centimeters, for example at least 4 centimeters, in particular at least 5 centimeters long along the column axis of the column-shaped section.

At least one embodiment of the invention further relates to a medical system for imaging and/or intervention, having the operating device according to one of the disclosed embodiments and the holding structure for the operating device.

The medical system may, for example, have a patient couch for the recumbent positioning of a patient. The holding structure may, for example, be arranged on the patient couch or integrated into the patient couch. For example, the operating device may be configured for operating the patient couch, in particular for remotely controlling the patient couch.

It may furthermore be provided that the medical system has a trolley, for example in the form of a medical equipment cart. The holding structure may, for example, be arranged on the trolley or integrated into the trolley. For example, the operating device may be configured for operating the trolley, in particular for remotely controlling the trolley.

The medical system may, for example, have a medical imaging device and/or a medical intervention device. The operating device may, for example, be configured for operating the medical imaging device, in particular for remotely controlling the medical imaging device, and/or for operating the medical intervention device, in particular for remotely controlling the medical intervention device.

The medical imaging device may, for example, be chosen from the group of imaging modalities which consists of an X-ray device, a C-arm X-ray device, a computed tomography device (CT device), a molecular imaging device (MI device), a single-photon emission computed tomography device (SPECT device), a positron emission tomography device (PET device), a magnetic resonance tomography device (MR device) and combinations thereof, in particular a PET-CT device and a PET-MR device. The medical imaging device may further have a combination of an imaging modality, which is selected from the group of imaging modalities for example, and an irradiation modality. In this context, the irradiation modality may, for example, have an irradiation unit for therapeutic irradiation.

The medical system may, in particular, have a data transfer connection and/or a power transfer connection. For example, the releasable connection may have the data transfer connection and/or the power transfer connection.

The data transfer connection may, for example, be configured to transfer data between the operating device and a data transfer interface of the medical system. In particular, the data transfer connection may be bidirectional. The data transfer interface of the medical system may, in particular, be integrated into the holding structure.

The power transfer connection may, for example, be configured to transfer power from a power supply interface of the medical system to the operating device. The power supply interface of the medical system may, in particular, be integrated into the holding structure.

One embodiment provides that the connecting unit has a first connecting element and a second connecting element for clamping the holding structure between the first connecting element and the second connecting element, wherein the releasable connection is based on the clamping of the holding structure between the first connecting element and the second connecting element.

One embodiment provides that the first connecting element is arranged such that it cannot move relative to the housing of the operating device, wherein the first connecting element and the second connecting element, during the one-handed gripping of the grip region, are arranged relative to one another such that a positive connection between the first connecting element and the holding structure and a gap between the second connecting element and the holding structure can be formed at the same time, wherein the connecting unit is configured such that letting go of the grip region causes a closing of the gap between the second connecting element and the holding structure, while forming a positive connection between the second connecting element and the holding structure and retaining the positive connection between the first connecting element and the holding structure.

In particular, the clamping of the holding structure between the first connecting element and the first connecting element may be based on the positive connection between the second connecting element and the holding structure and the positive connection between the second connecting element and the holding structure.

One embodiment provides that the holding structure is embodied in the form of a rail, wherein the holding structure has a plurality of connecting points, which are arranged successively along the rail, in particular are arranged successively in a continuous manner, wherein each connecting point of the plurality of connecting points is suitable for the releasable connection of the connecting unit to the holding structure at the connecting point.

It may furthermore be provided that the operating device can be displaced along the rail, while retaining the positive connection between the first connecting element and the holding structure, when the releasable connection is released.

One embodiment provides that the medical system further has a patient couch for the recumbent positioning of a patient. In particular, the longitudinal direction of the patient couch may be substantially horizontal, in particular horizontal.

One embodiment provides that the holding structure is arranged substantially parallel, in particular parallel, with a longitudinal direction of the patient couch.

One embodiment provides that the patient couch has a couch frame and a couch board, wherein the couch board is configured for the recumbent accommodation of the patient and is mounted via the couch frame such that it can move relative to the couch frame, wherein the holding structure is arranged on the couch frame.

In particular, the couch board may be mounted via the couch frame such that it can move along the longitudinal direction of the patient couch relative to the couch frame.

One embodiment provides that a vertical position of the holding structure is located below a vertical position of an edge region of the patient couch, wherein the edge region of the patient couch protrudes horizontally beyond the holding structure, wherein the connecting unit protrudes horizontally beyond a region of the operating device that is located at the vertical position of the edge region of the patient couch when the releasable connection between the connecting unit and the holding structure is established.

A vertical position may, in particular be a position in relation to a vertical coordinate axis and/or a spacing from a horizontal reference plane, for example a height above a horizontal floor.

In particular, a vertical position of the connecting unit may be located below a vertical position of the region of the operating device that is located at the vertical position of the edge region of the patient couch when the releasable connection between the connecting unit and the holding structure is established.

In particular, a vertical position of an edge region of the operating device may be located above the vertical position of the region of the operating device that is located at the vertical position of the edge region of the patient couch when the releasable connection between the connecting unit and the holding structure is established.

It may furthermore be provided that the edge region of the operating device protrudes horizontally beyond the region of the operating device that is located at the vertical position of the edge region of the patient couch when the releasable connection between the connecting unit and the holding structure is established, for example protrudes substantially in parallel with the connecting unit such that the operating device surrounds the edge region of the patient couch at least approximately in a U-shaped manner, in particular substantially in a U-shaped manner, and/or surrounds it such that a notional vertical axis intersects the edge region of the operating device, the edge region of the patient couch and the connecting unit.

It may furthermore be provided that the connecting unit forms a first leg of a U-shape, that the edge region of the operating device forms a second leg of the U-shape and that the region of the operating device that is located at the vertical position of the edge region of the patient couch when the releasable connection between the connecting unit and the holding structure is established forms an apex region of the U-shape, wherein the apex region of the U-shape is located between the first leg of the U-shape and the second leg of the U-shape. The operating device may have at least one further region that is not included in the U-shape. For example, the grip region may be a region of the operating device that is not included in the U-shape.

It may furthermore be provided that the column-shaped section is arranged between the region of the operating device that is located at the vertical position of the edge region of the patient couch, when the releasable connection between the connecting unit and the holding structure is established, and the connecting unit. It may furthermore be provided that the direction that is substantially parallel, in particular is parallel with the column axis of the column-shaped section is vertical.

One embodiment provides that the operating device has an operating element for operating the medical system, wherein the operating element is located at a vertical position of the patient when the patient is positioned in a recumbent manner via the patient couch and the releasable connection between the connecting unit and the holding structure is established.

The operating element may, for example, be a joystick, in particular an intervention joystick. In particular, the medical system may be configured for controlling a movement of the couch board based on a manual user input detected via the operating element.

It may furthermore be provided that the operating element is deactivated automatically when the releasable connection is released and/or that the operating element is activated automatically when the releasable connection is established.

It may furthermore be provided that at least one subregion of the grip region, in particular the grip region, is located at the vertical position of the patient when the patient is positioned in a recumbent manner via the patient couch and the releasable connection between the connecting unit and the holding structure is established.

By way of an attachment of the grip region and/or the operating element that is elevated relative to the connecting unit, it is possible for an ergonomically advantageous use of the operating device, in particular on a patient couch, to be supported.

FIG. 1 shows the operating device 1 for the medical system 2 for imaging and/or intervention. The operating device 1 has a housing G, a grip region B, a coupling unit K and a connecting unit V.

The connecting unit V is configured for releasably connecting to a holding structure S for the operating device 1 and, via the coupling unit K, is coupled to the grip region B such that a releasing of the releasable connection is caused by gripping the grip region B with one hand and an establishing of the releasable connection is caused by letting go of the grip region B.

The grip region B is embodied such that the operating device 1 can be carried in one hand by gripping the grip region B with one hand.

The operating device 1 further has a lever H that is mounted such that it can pivot relative to the housing G. The grip region B has a region of the housing G and a region of the lever H, which are arranged relative to one another such that gripping the grip region B with one hand causes a pivoting of the region of the lever H toward the region of the housing G. The connecting unit V is coupled to the grip region B via the coupling unit K such that, by pivoting the region of the lever toward the region of the housing G, a force is exerted on the connecting unit V which causes the releasing of the releasable connection.

The region of the housing G has a contact area D such that, when the grip region B is gripped with one hand, a thumb of a hand is pressed against the contact area D and at least one finger of the hand opposite the thumb of the hand is pressed against the region of the lever H.

The operating device 1 further has a column-shaped section L, wherein the grip region B and the connecting unit V are interconnected via the column-shaped section L such that the grip region B and the connecting unit V are spaced apart from one another in relation to a direction y that is substantially parallel with a column axis of the column-shaped section L.

Figure 2:
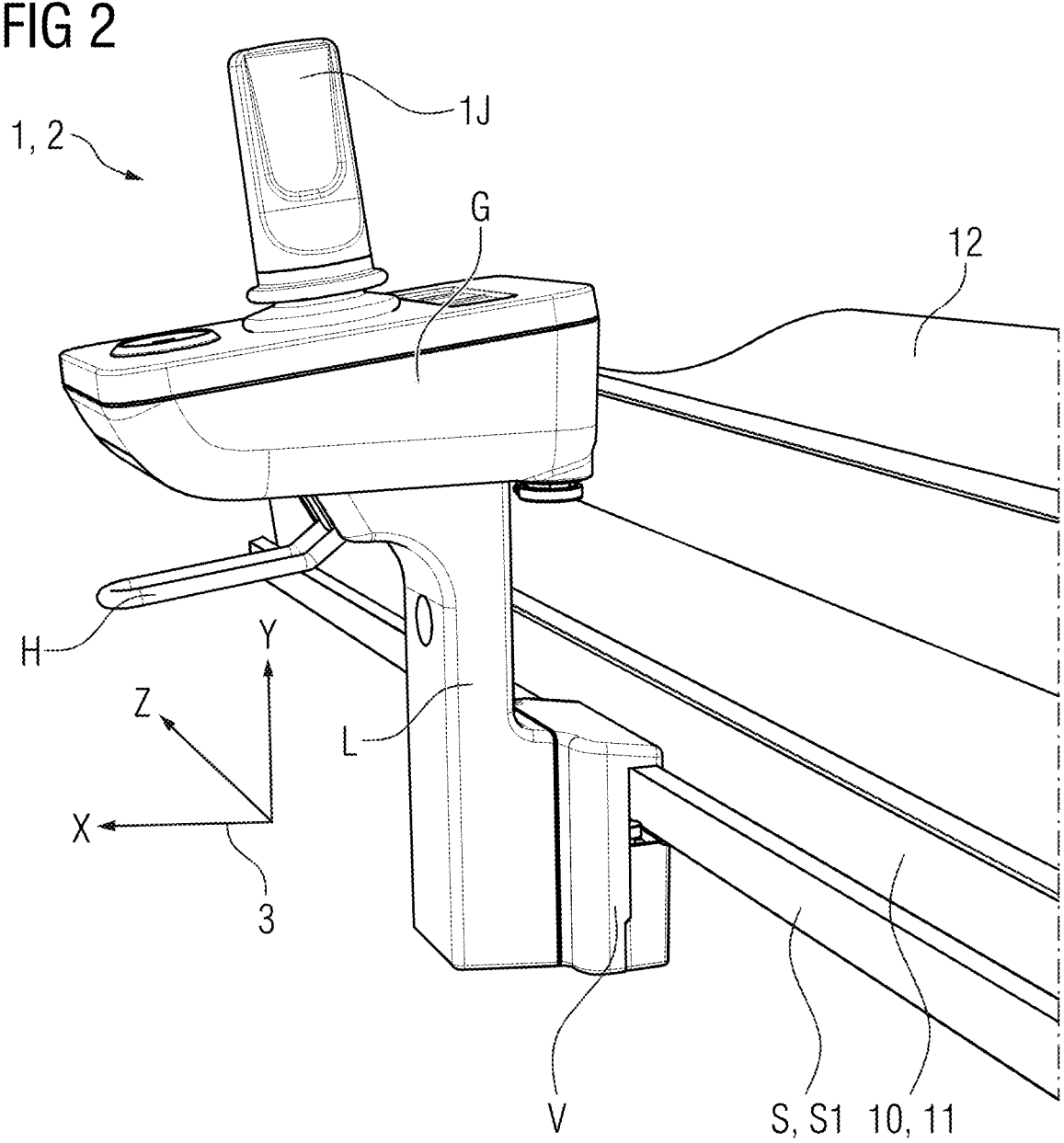
FIG. 2 shows a medical system for imaging and/or intervention with a patient couch.

FIG. 2 shows the medical system 2 for imaging and/or intervention, having the operating device 1, the holding structure S for the operating device 1 and the patient couch 10 for the recumbent positioning of the patient 13.

The patient couch 10 has a couch frame 11 and a couch board 12, wherein the couch board 12 is configured for the recumbent positioning of the patient 13 and is mounted via the couch frame 11 such that it can move relative to the couch frame 11, wherein the holding structure S is arranged on the couch frame 11.

The holding structure S is arranged substantially parallel with a longitudinal direction z of the patient couch 10. The holding structure S is embodied in the form of a rail S1, wherein the holding structure S has a plurality of connecting points, which are arranged successively along the rail S1, in particular are arranged successively in a continuous manner, wherein each connecting point of the plurality of connecting points is suitable for the releasable connection of the connecting unit V to the holding structure S at the connecting point.

The operating device 1 can be displaced along the rail S1, while retaining the positive connection between the first connecting element V1 and the holding structure S, when the releasable connection is released.

The direction y is vertical and substantially parallel with the column axis of the column-shaped section L. The longitudinal direction z of the patient couch 10 is horizontal. The transverse direction x of the patient couch is horizontal and perpendicular to the longitudinal direction z.

The rectangular coordinate system 3 has a first horizontal coordinate axis parallel with the transverse direction x of the patient couch 10, a vertical coordinate axis parallel with the direction y and a second horizontal coordinate axis parallel with the longitudinal direction z of the patient couch 10.

The operating device 1 has an operating element 1J for operating the medical system 2, wherein the operating element 1J is located at a vertical position of the patient 13 when the patient 13 is positioned in a recumbent manner via the patient couch 10 and the releasable connection between the connecting unit V and the holding structure S is established.

Figure 3:
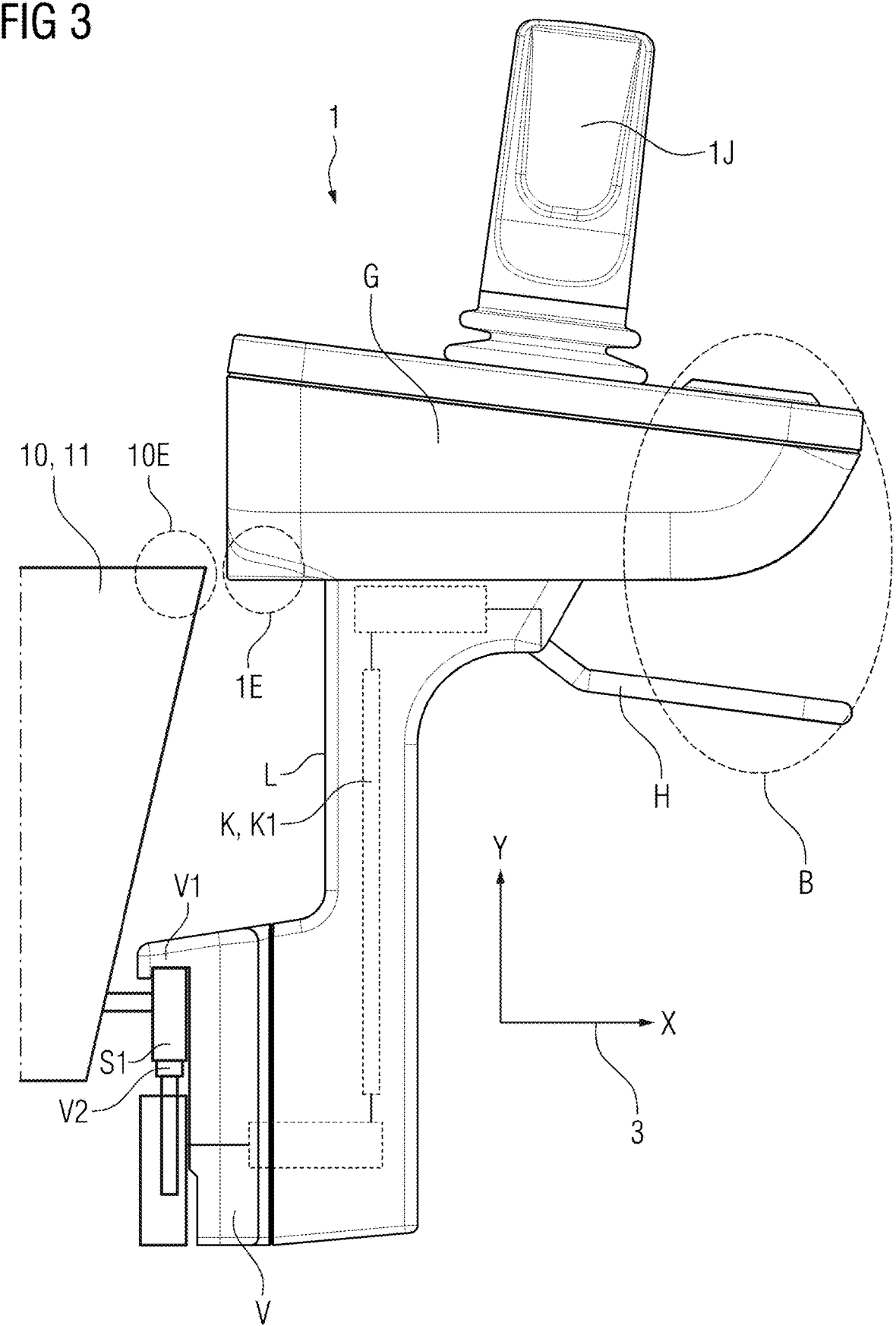
FIG. 3 shows the operating device in an operating state in which the releasable connection is established.

FIG. 3 shows the operating device 1 in an operating state in which the releasable connection is established.

The releasable connection is a releasable clamp connection. The coupling unit K is embodied for mechanical force transfer from the grip region B to the connecting unit V and has the linkage K1.

The connecting unit V has a first connecting element V1 and a second connecting element V2 for clamping the holding structure S between the first connecting element V1 and the second connecting element V2, wherein the releasable connection is based on the clamping of the holding structure S between the first connecting element V1 and the second connecting element V2.

The first connecting element V1 is arranged such that it cannot move relative to the housing G of the operating device 1. The first connecting element V1 and the second connecting element V2, during the one-handed gripping of the grip region B, are arranged relative to one another such that a positive connection between the first connecting element V1 and the holding structure S and a gap V0 between the second connecting element V2 and the holding structure S can be formed at the same time, wherein the connecting unit V is configured such that letting go of the grip region B causes a closing of the gap V0 between the second connecting element V2 and the holding structure S, while forming a positive connection between the second connecting element V2 and the holding structure S and retaining the positive connection between the first connecting element V1 and the holding structure S.

The second connecting element V2 is embodied in the form of a plunger, which can be pressed against the rail S1 from below.

A vertical position of the holding structure S is located below a vertical position of an edge region 10E of the patient couch 10, wherein the edge region 10E of the patient couch 10 protrudes horizontally beyond the holding structure S, wherein the connecting unit V protrudes horizontally beyond a region 1E of the operating device 1 that is located at the vertical position of the edge region 10E of the patient couch 10 when the releasable connection between the connecting unit V and the holding structure S is established.

Figure 4:
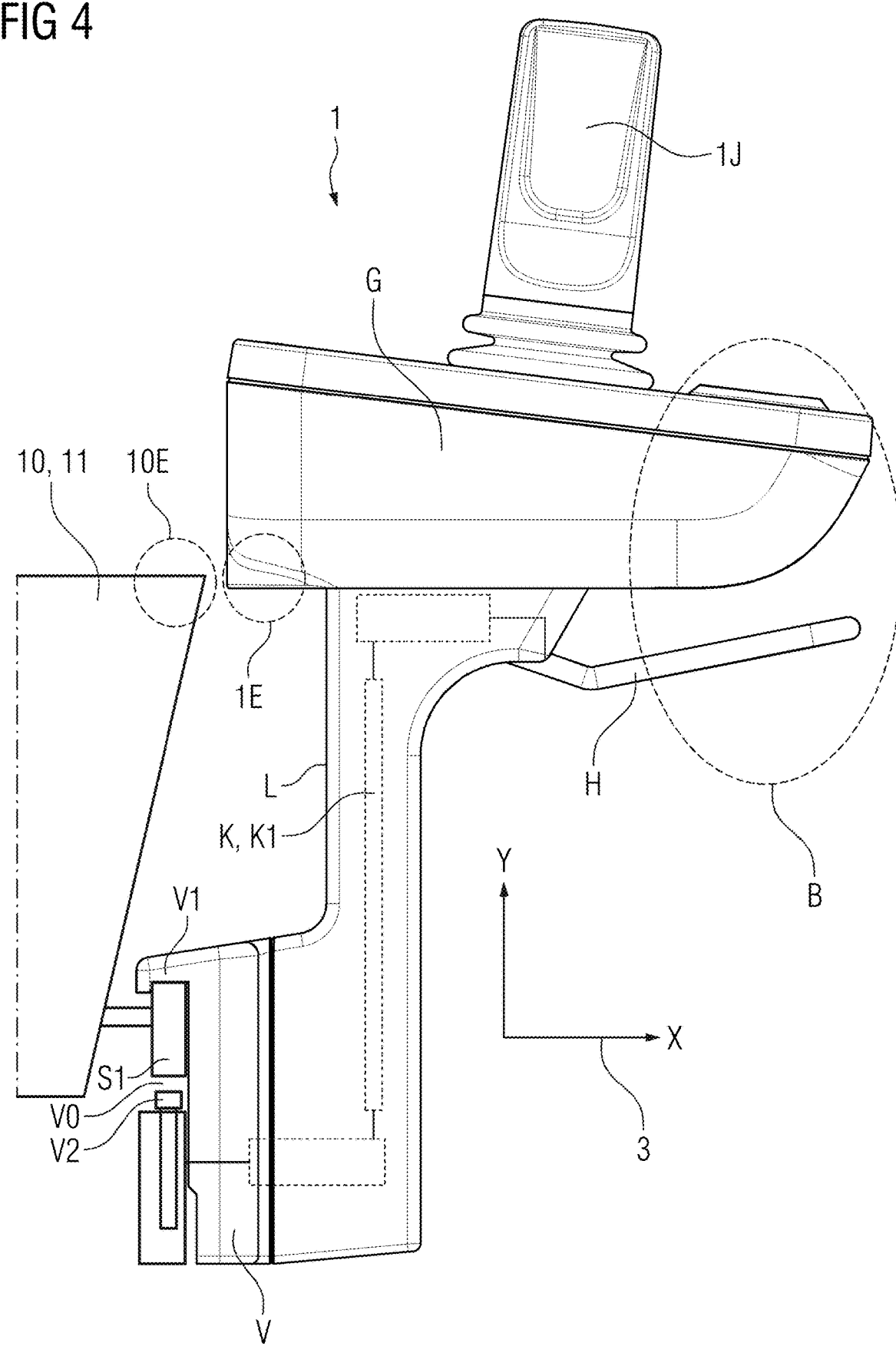
FIG. 4 shows the operating device in an operating state in which the releasable connection is released.

FIG. 4 shows the operating device 1 in an operating state in which the releasable connection is released.

Figure 5:
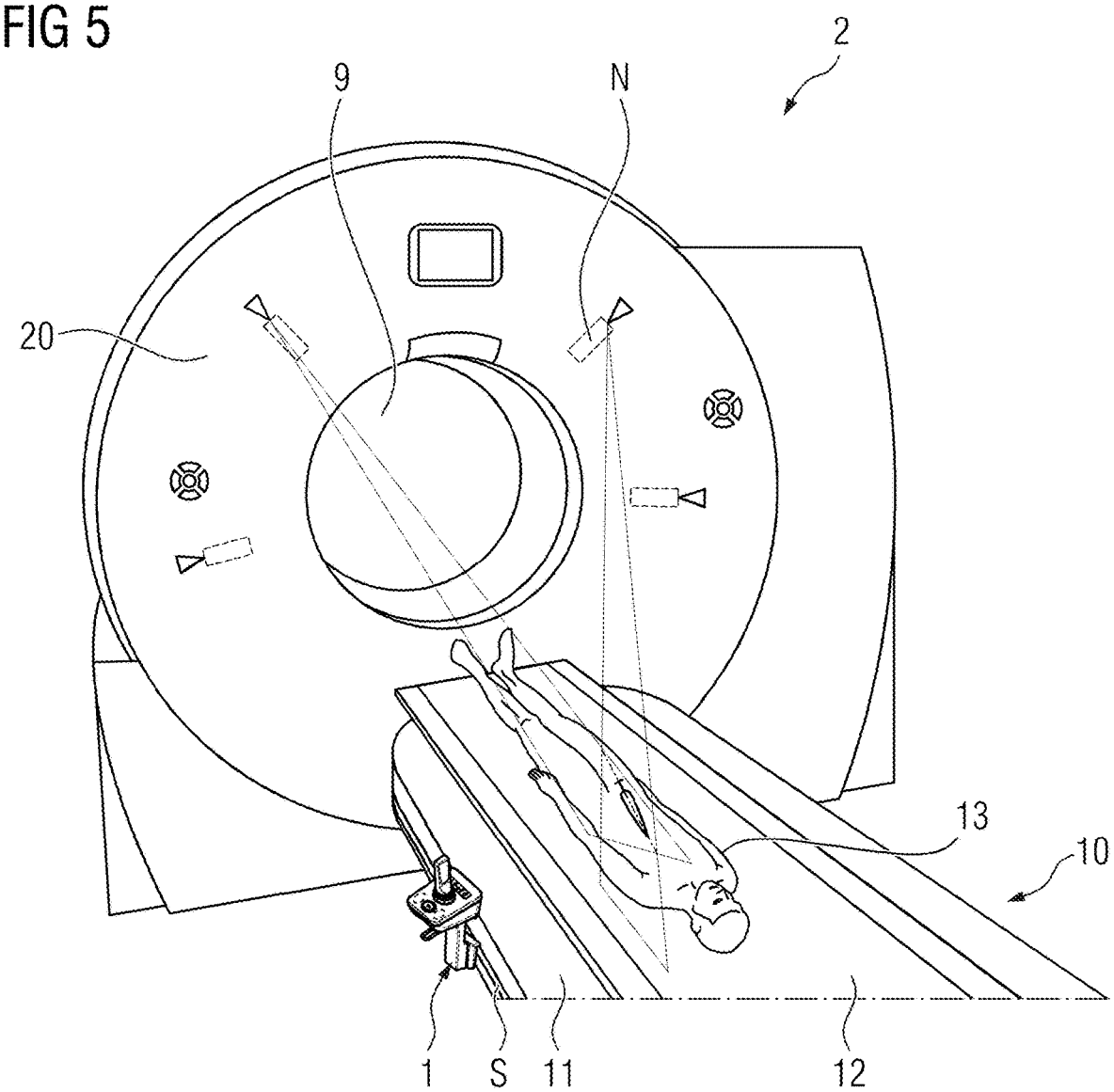
FIG. 5 shows a medical system for imaging and/or intervention with a patient couch and a medical imaging device.

FIG. 5 shows the medical system 2 for imaging and/or intervention, having the operating device 1, the holding structure S for the operating device 1, the patient couch 10 for the recumbent positioning of the patient 13 and the medical imaging device 20. The medical imaging device 20 has a tunnel-shaped opening 9, in which the couch board 12 can be inserted along the longitudinal direction z of the patient couch 10. The medical imaging device 20 further has a laser navigation system N for the intervention.

What is claimed is:

1. An operating device for a medical system for at least one of imaging and intervention, comprising:
   a housing;
   a grip region;
   a coupling unit; and
   a connecting unit,
   wherein the connecting unit is configured to releasably connect to a holding structure for the operating device and, via the coupling unit, is coupled to the grip region such that a releasing of a releasable connection is caused by a gripping of the grip region with one hand of a person and an establishing of the releasable connection is caused by a letting go of the grip region, and
   wherein the grip region is configured for carrying of the operating device by the gripping of the grip region with the one hand of the person.

2. The operating device of claim 1, wherein the connecting unit includes the releasable connection and wherein the releasable connection is a releasable clamp connection.

3. The operating device of claim 2, further comprising:
   a lever, mounted to be pivotable relative to the housing,
   wherein the grip region includes a region of the housing and a region of the lever, arranged relative to one another such that the gripping of the grip region with the one hand causes a pivoting of the region of the lever toward the region of the housing, and
   wherein the connecting unit is coupled to the grip region via the coupling unit such that, by pivoting the region of the lever toward the region of the housing, a force is exerted on the connecting unit which causes the releasing of the releasable connection.

4. The operating device of claim 2, wherein the coupling unit is embodied for mechanical force transfer from the grip region to the connecting unit.

5. The operating device of claim 2, wherein the coupling unit includes a linkage.

6. The operating device of claim 2, further comprising:
   a column-shaped section,
   wherein the grip region and the connecting unit are interconnected via the column-shaped section such that the grip region and the connecting unit are spaced apart from one another in relation to a direction substantially parallel with a column axis of the column-shaped section.

7. The operating device of claim 1, further comprising:
   a lever, mounted to be pivotable relative to the housing,
   wherein the grip region includes a region of the housing and a region of the lever, arranged relative to one another such that the gripping of the grip region with the one hand causes a pivoting of the region of the lever toward the region of the housing, and
   wherein the connecting unit is coupled to the grip region via the coupling unit such that, by pivoting the region of the lever toward the region of the housing, a force is exerted on the connecting unit which causes the releasing of the releasable connection.

8. The operating device of claim 1, wherein the coupling unit is embodied for mechanical force transfer from the grip region to the connecting unit.

9. The operating device of claim 1, wherein the coupling unit includes a linkage.

10. The operating device of claim 1, further comprising:
    a column-shaped section,
    wherein the grip region and the connecting unit are interconnected via the column-shaped section such that the grip region and the connecting unit are spaced apart from one another in relation to a direction substantially parallel with a column axis of the column-shaped section.

11. A medical system for at least one of imaging and intervention, comprising:
    the operating device of claim 1; and
    the holding structure for the operating device.

12. The medical system of claim 11,
    wherein the connecting unit includes a first connecting element and a second connecting element, configured to clamp the holding structure between the first connecting element and the second connecting element, and
    wherein the releasable connection is based on clamping of the holding structure between the first connecting element and the second connecting element.

13. The medical system of claim 12,
    wherein the first connecting element is arranged to not be moveable relative to the housing of the operating device,
    wherein the first connecting element and the second connecting element, during the gripping of the grip region with the one hand, are arranged relative to one another such that a positive connection between the first connecting element and the holding structure and a gap between the second connecting element and the holding structure is formable at a same time, and
    wherein the connecting unit is configured to
        cause a closing of the gap between the second connecting element and the holding structure upon letting go of the grip region, and
        form a positive connection between the second connecting element and the holding structure and retain the positive connection between the first connecting element and the holding structure.

14. The medical system of claim 12,
wherein the holding structure is embodied in a form of a rail,
wherein the holding structure includes a plurality of connecting points, arranged successively along the rail, and
wherein each respective connecting point of the plurality of connecting points is suitable for the releasable connection of the connecting unit and the holding structure at the respective connecting point.

15. The medical system of claim 12, further comprising:
a patient couch for recumbent positioning of a patient.

16. The medical system of claim 11,
wherein the holding structure is embodied in a form of a rail,
wherein the holding structure includes a plurality of connecting points, arranged successively along the rail, and
wherein each respective connecting point of the plurality of connecting points is suitable for the releasable connection of the connecting unit and the holding structure at the respective connecting point.

17. The medical system of claim 11, further comprising:
a patient couch for recumbent positioning of a patient.

18. The medical system of claim 17, wherein the holding structure is arranged substantially parallel with a longitudinal direction of the patient couch.

19. The medical system of claim 18,
wherein the patient couch includes a couch frame and a couch board,
wherein the couch board is configured for recumbent accommodation of the patient and is mounted via the couch frame to be movable relative to the couch frame, and
wherein the holding structure is arranged on the couch frame.

20. The medical system of claim 18,
wherein a vertical position of the holding structure is located below a vertical position of an edge region of the patient couch,
wherein the edge region of the patient couch is configured to protrude horizontally beyond the holding structure, and
wherein the connecting unit is configured to protrude horizontally beyond a region of the operating device located at the vertical position of the edge region of the patient couch when the releasable connection between the connecting unit and the holding structure is established.

21. The medical system of claim 18,
wherein the operating device includes an operating element to operate the medical system, and
wherein the operating element is located at a vertical position of the patient when the patient is positioned in a recumbent manner via the patient couch and the releasable connection between the connecting unit and the holding structure is established.

22. The medical system of claim 17,
wherein the patient couch includes a couch frame and a couch board,
wherein the couch board is configured for recumbent accommodation of the patient and is mounted via the couch frame to be movable relative to the couch frame, and
wherein the holding structure is arranged on the couch frame.

23. The medical system of claim 17,
wherein a vertical position of the holding structure is located below a vertical position of an edge region of the patient couch,
wherein the edge region of the patient couch is configured to protrude horizontally beyond the holding structure, and
wherein the connecting unit is configured to protrude horizontally beyond a region of the operating device located at the vertical position of the edge region of the patient couch when the releasable connection between the connecting unit and the holding structure is established.

24. The medical system of claim 17,
wherein the operating device includes an operating element to operate the medical system, and
wherein the operating element is located at a vertical position of the patient when the patient is positioned in a recumbent manner via the patient couch and the releasable connection between the connecting unit and the holding structure is established.

* * * * *